(12) United States Patent
Yasuhara et al.

(10) Patent No.: US 6,537,822 B1
(45) Date of Patent: Mar. 25, 2003

(54) METHOD FOR ANALYZING FREE FLUORINE IN SOLUTIONS CONTAINING HYDROFLUORIC ACID SOLUTION, AND APPARATUS FOR PRACTICING THE METHOD

(75) Inventors: Hisao Yasuhara, Chiba (JP); Makoto Shimura, Chiba (JP)

(73) Assignee: Kawasaki Steel Corporation, Hyogo (JP)

(*) Notice: Subject to any disclaimer, the term of this patent is extended or adjusted under 35 U.S.C. 154(b) by 198 days.

(21) Appl. No.: 09/610,387

(22) Filed: Jul. 5, 2000

(30) Foreign Application Priority Data

Jul. 6, 1999 (JP) ............................. 11-191427

(51) Int. Cl.$^7$ ............................................ G01N 33/00
(52) U.S. Cl. .................... 436/124; 436/163; 422/75; 422/76; 422/77
(58) Field of Search ................... 436/124, 163; 422/75–77

(56) References Cited

U.S. PATENT DOCUMENTS 4,775,973 A  * 10/1988  Paul ......................... 250/373

5,286,358 A  2/1994  Fletcher, III et al.
5,518,933 A  5/1996  Ishibashi

FOREIGN PATENT DOCUMENTS

| EP | 0161658 A2 | 11/1985 |
|---|---|---|
| JP | 3199386 | 8/1991 |
| JP | 05263279 A | * 10/1993 |
| JP | 7294509 | 11/1995 |
| JP | 07294509 A | * 11/1995 |

* cited by examiner

Primary Examiner—Jill Warden
Assistant Examiner—Yelena Gakh
(74) Attorney, Agent, or Firm—Young & Thompson

(57) ABSTRACT

Free fluorine is measured in a hydrofluoric acid-containing solution with a coexistent metallic ion based on a total fluorine concentration, a total acid concentration, a metallic ion concentration, the equilibrium constant of hydrofluoric acid, and equilibrium constants of metal fluoride complexes. It is possible to accurately analyze free fluorine in a hydrofluoric acid-containing solution without being affected by a coexistent metal and by the passage of time. This technique may be used to accurately control the concentration of free fluorine in a hydrofluoric acid-containing mixed acid pickling solution at the production site of a stainless steel so that improvement in descaling capability as well as reduction in the amount of chemical materials can be achieved.

7 Claims, 2 Drawing Sheets

METHOD FOR ANALYZING FREE FLUORINE IN SOLUTIONS CONTAINING HYDROFLUORIC ACID SOLUTION, AND APPARATUS FOR PRACTICING THE METHOD

BACKGROUND OF THE INVENTION

1. Field of the Invention

The present invention relates to a method for analyzing free fluorine in solutions containing hydrofluoric acid, and an analytical apparatus therefor. More specifically, the present invention relates to a method for analyzing free fluorine in solutions containing both hydrofluoric acid and metal ions, which enables analyzing free fluorine without being affected by the coexistent metallic ion, and an analytical apparatus therefor.

2. Description of the Related Art

Stainless steel is used in various applications for its excellent corrosion resistance and appearance. Such steel is subjected, after hot rolling, to a pickling treatment to remove scales (oxidized film) formed on its surface layer. A hydrofluoric acid-containing solution such as an aqueous mixed acid solution of nitric acid and hydrofluoric acid is widely used as a pickling solution because of the excellent descaling capability.

Component analysis of the pickling solution is important, as the pickling efficiency varies as a function of the acid consumption during pickling, and as a function of dissolution of iron ions into the pickling solution.

Consequently, the hydrofluoric acid concentration, the total acid concentration (hydrofluoric acid concentration plus nitric acid concentration) as well as the metallic ion concentration (iron ion concentration) are analyzed in consideration of the influence on the descaling capability when controlling the concentration of the above-described pickling solution for a stainless steel.

Also, in this case, it is important to control, as an indicator of hydrofluoric acid concentration, the concentration of free fluorine on which the descaling capability is dependent, that is, the concentration of effective fluorine (the sum of HF concentration plus $F^-$ concentration) which is not combined with iron or the like.

As a method for analyzing nitric acid/hydrofluoric acid for use in pickling, a method for analyzing hydrofluoric acid concentration and nitric acid concentration using an ionic electrode was reported (cf. CAMP-ISIJ, Vol. 8 (1995), p. 1980).

However, the above-mentioned method is affected by the coexistent components as their concentrations vary. In addition, the analytical accuracy is not sufficient.

Also, a method for analyzing hydrofluoric acid by titration using lanthanum nitrate or the like was reported (cf. CAMP-ISIJ, Vol. 6 (1993), p. 1311). The method is, however, dedicated to the analysis of total fluorine concentration, and cannot be applied to analyzing free fluorine which is effective for descaling.

Also, an analytical method for analyzing acids and metals according to their forms by thermometric titration and potentiometric titration was reported in the Japanese Unexamined Patent Application Publication No. 3-15749. The method is, however, inappropriate for an analytical method of total free fluorine, since it is not possible to analyze fluorine ion in solution.

An analytical method for analyzing free fluorine by the iron-acetylacetone complex fading absorptiometric method was also reported (J. P. McKaveney: Anal. Chem. Vol. 40 (1968), p. 1276).

However, in the above-described cases, it is difficult to perform analysis in a stable manner, as the absorbance changes with the passage of time, if a metallic ion such as iron ion coexists in a solution as in a pickling solution for a stainless steel, as stated later.

SUMMARY OF THE INVENTION

The present invention aims at solving problems of the above-described conventional techniques and providing a method for analyzing free fluorine in a hydrofluoric acid-containing solution which enables analyzing free fluorine without being affected by a coexisting metal and with excellent accuracy, and an analytical apparatus therefor.

Thus, the present invention is a method for analyzing free fluorine in a hydrofluoric acid-containing solution with a coexistent metallic ion wherein the concentration of free fluorine is determined based on a total fluorine concentration, a total acid concentration, a metallic ion concentration, the equilibrium constant of hydrofluoric acid, and equilibrium constants of metal fluoride complexes. It is noted that this analytical method is a method for analyzing free fluorine suitable for the case in which a hydrofluoric acid-containing solution with a coexistent metallic ion is a pickling solution for a stainless steel.

Also, the present invention provides an apparatus for analyzing free fluorine in a hydrofluoric acid-containing solution with a coexistent metallic ion comprising:

a total fluorine concentration analyzing unit for analyzing a total fluorine concentration in the above-described solution to output the analytical value;

a total acid concentration analyzing unit for analyzing a total acid concentration in the above-described solution to output the analytical value;

a metallic ion concentration analyzing unit for analyzing a metallic ion concentration in the above-described solution to output the analytical value; and a processing unit for inputting each of the outputs from the analyzing units to calculate the concentration of the above described free fluorine based on the equilibrium constants of hydrofluoric acid and metal fluoride complexes.

In this apparatus for analyzing free fluorine, it is preferable that the above-described total fluorine concentration analyzing unit is an analytical unit employing a precipitation titration method using lanthanum nitrate, the above-described total acid concentration analyzing unit is an analytical unit for reducing a metal followed by neutralization titration, and the above-described metallic ion concentration analyzing unit is a unit for analyzing a metal-EDTA complex by absorptiometry.

More preferably, the above-described apparatus for analyzing free fluorine is further equipped with a fractionating unit to supply a sample to each of the units for analyzing total fluorine concentration, total acid concentration and metallic ion concentration.

DESCRIPTION OF THE PREFERRED EMBODIMENTS

The present invention will be explained in greater detail below.

The present invention provides a method for analyzing free fluorine in a hydrofluoric acid-containing solution with a coexistent metallic ion wherein the concentration of free fluorine is determined based on a total fluorine concentration, a total acid concentration, a metallic ion concentration, the equilibrium constant of hydrofluoric acid, and equilibrium constants of metal fluoride complexes, and an analytical apparatus therefor.

Here, the free fluorine concentration stated above is the sum of a hydrogen fluoride concentration and a fluorine ion concentration, that is, an ($HF+F^-$) concentration.

Figure 1:
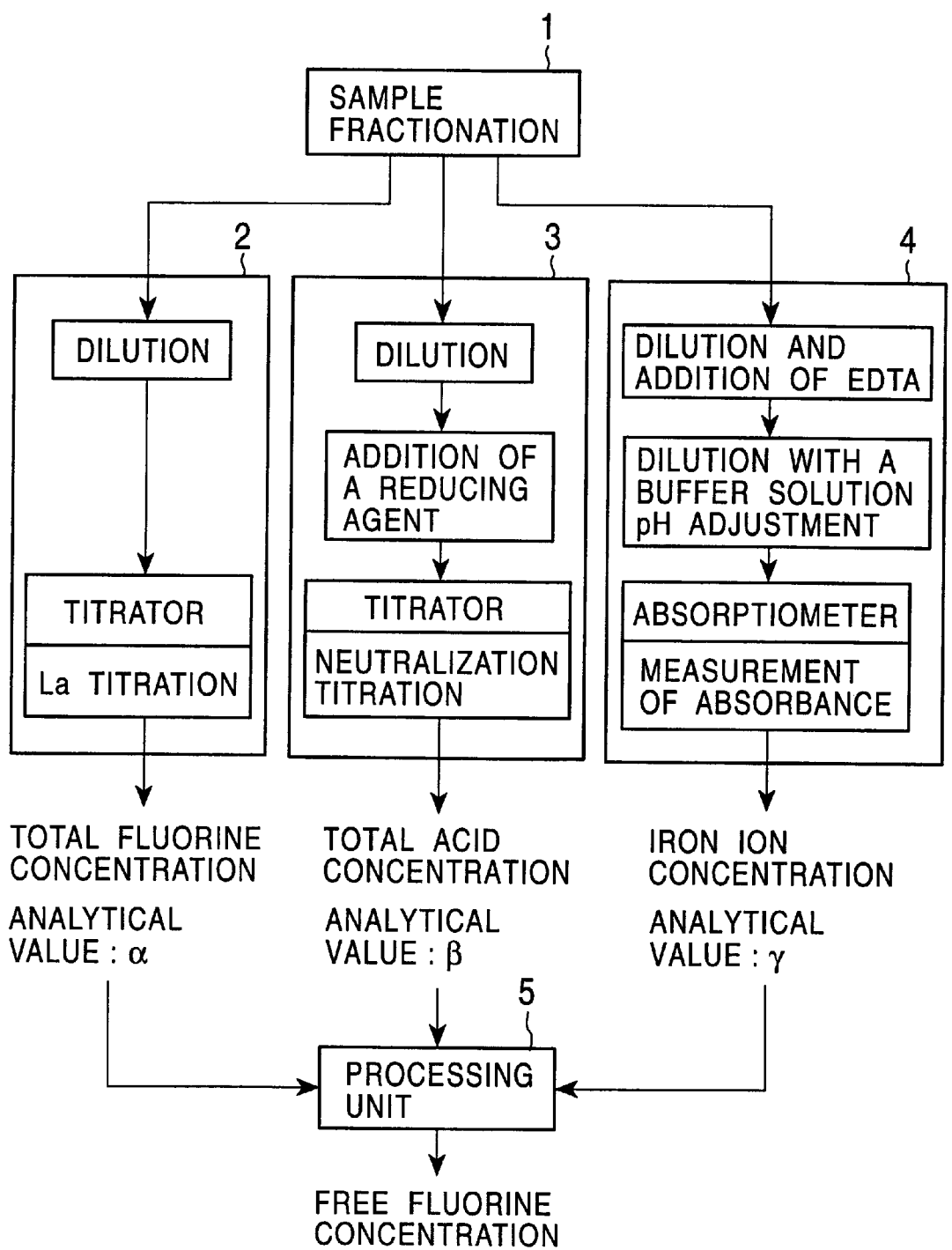
FIG. 1 is a flow chart showing an example of an analytical method for analyzing free fluorine according to the present invention and an example of an analytical apparatus therefor.

Hereinafter, analysis of free fluorine in a hydrofluoric acid-containing pickling solution for a stainless steel will be explained as an example to help understand the present invention. FIG. 1 is a flow chart to illustrate the method and the analytical apparatus.

In a pickling line for a stainless steel, a sample is taken from the hydrofluoric acid-containing pickling solution in a pickling vessel by a sample fractionating unit 1, and is sent to a total fluorine concentration analyzing unit 2, to a total acid concentration analyzing unit 3 and also to a metallic ion concentration analyzing unit 4 (an iron ion concentration analyzing unit is shown in FIG. 1). Thus, from the hydrofluoric acid-containing solution with a coexistent iron ion, the total fluorine concentration analyzing unit 2, the total acid concentration analyzing unit 3, the iron ion concentration analyzing unit 4 provide a total fluorine concentration (mol/L): $\alpha$; a total acid concentration (mol/L): $\beta$; and an iron ion concentration (mol/L): $\gamma$; respectively. These analytical values are outputted to a processing unit 5. In the processing unit 5, the free fluorine concentration, or the sum of hydrogen fluoride concentration and fluorine ion concentration ($[HF]+[F^-]$) (mol/L) is determined by calculation based on these analytical values: $\alpha$, $\beta$ and $\gamma$, as well as the equilibrium constant of hydrofluoric acid: K, and the equilibrium constants of iron fluoride complexes: $K_1$ and $K_2$, the constants being stored beforehand in the processing unit 5.

The following are explanations of the method for analyzing total fluorine concentration, total acid concentration and iron ion concentration using the total fluorine concentration analyzing unit 2, the total acid concentration analyzing unit 3, and the metallic ion (iron ion) concentration analyzing unit 4.

The total fluorine concentration analyzing unit 2 is an analytical unit utilizing the lanthanum nitrate precipitation titration method. Accordingly, a sample of solution is diluted by adding pure water, and then is subjected to titration by adding lanthanum nitrate to determine the total fluorine concentration.

The total acid concentration analyzing unit 3 analyzes total acid concentration by the iron reduction-neutralization titration method. Accordingly, to a sample of solution, pure water is added for dilution followed by addition of a reducing agent to change $Fe^{3+}$ into $Fe^{2+}$ in the solution, and then the mixture is subjected to neutralization titration. Sodium isoascorbate is an example of a reducing agent which can be used for this purpose.

The iron ion concentration analyzing unit 4 is an analytical unit using the iron-EDTA complex absorptiometric method. Accordingly, to a sample of solution, an aqueous EDTA solution is first added for dilution, and then a buffer solution (pH: 7) is added to form an iron-EDTA complex in a stable manner. The mixture is then diluted to a specific volume, and is subjected to the measurement of absorbance in a UV range (ex. 350 nm).

It is noted that in each of the above-described analyzing units, dilution of a solution sample, addition of a reducing agent, an aqueous EDTA solution and a buffer solution to the sampled solution, transfer of the sampled solution thus obtained to a titrator and an absorptiometer, as well as the analyses, are automatically performed.

It is preferable in the present invention to use titrators when analyzing total fluorine concentration and total acid concentration, and to use an absorptiometer when analyzing the concentration of a metallic ion such as iron ion, since they can furnish simple and quick analysis.

However, it is also possible to use other analytical methods and other analyzing units when analyzing each component.

Next, the processing method for calculating a free fluorine concentration by the processing unit 5 will be explained.

The processing unit 5 functions to obtain a free fluorine concentration ($[HF]+[F^-]$) (mol/L) by calculation through solving the following simultaneous equations (1)–(6).

Thus, with the processing unit 5, the concentration of free fluorine ($[HF]+[F^-]$) (mol/L) which is not combined with iron or the like is obtained by calculation through solving the following simultaneous equations (1)–(6) using an analytical value of total fluorine concentration $\alpha$, an analytical value of total acid concentration $\beta$ and an analytical value of iron ion concentration $\gamma$, the values having been obtained with the respective analyzing units, as well as the equilibrium constant K of hydrofluoric acid and the equilibrium constants $K_1$ and $K_2$ of iron fluoride complexes, the constants having been previously stored in the processing unit 5.

$$[HF]/([H^+]\times[F^-])=K \tag{1}$$

$$[FeF^{2+}]/([Fe^{3+}]\times[F^-])=K_1 \tag{2}$$

$$[FeF_2^+]/([FeF^{2+}]\times[F^-])=K_2 \tag{3}$$

$$[HF]+[F^-]+[FeF^{2+}]+2[FeF_2^+]=\alpha \tag{4}$$

$$[HF]+[H^+]=\beta \tag{5}$$

$$[Fe^{3+}]+[FeF^{2+}]+[FeF_2^+]=\gamma \tag{6}$$

In the above-described equations (1)–(6),

K is the equilibrium constant of the following reaction formula (7), $K_1$ is the equilibrium constant of the following reaction formula (8), $K_2$ is the equilibrium constant of the following reaction formula (9), $\alpha$ is an analytical value of total fluorine concentration (mol/L), $\beta$ is an analytical value of total acid concentration (mol/L), and $\gamma$ is an analytical value of iron ion concentration (mol/L).

$$H^+ + F^- \leftrightarrow HF \tag{7}$$

$$Fe^{3+} + F^- \leftrightarrow FeF^{2+} \tag{8}$$

$$FeF^{2+} + F^- \leftrightarrow FeF_2^+ \tag{9}$$

Thus, the free fluorine concentration: $([HF]+[F^-])$ (mol/L) is obtained by solving the simultaneous equations (1)–(6), with [HF], [H$^+$], [F$^-$], [FeF$^{2+}$], [Fe$^{3+}$] and [FeF$_2^+$] as variables.

Here, known data of K, $K_1$ and $K_2$ derived from the following equations (10)–(12) are examples of values which can be used as the above-described equilibrium constant K of hydrofluoric acid and the equilibrium constants $K_1$ and $K_2$ of iron fluoride complexes (cf. Stability Constants of Metal-Ion Complexes, Special Publication No. 17, 1964).

$$\text{Log } K=2.9 \tag{10}$$

[where K is the equilibrium constant of the reaction formula (7)]

$$\text{Log } K_1=5.2 \tag{11}$$

[where $K_1$ is the equilibrium constant of the reaction formula (8)]

$$\text{Log } K_2=3.9 \tag{12}$$

[where $K_2$ is the equilibrium constant of the reaction formula (9)]

The processing unit for the free fluorine analyzing apparatus shown in FIG. 1 is a processing unit for obtaining a free fluorine concentration by calculation of the above-described equations (1)–(6), based on a total fluorine concentration, a total acid concentration and an iron ion concentration obtained with the titrator and the absorptiometer from a hydrofluoric acid-containing solution with a coexistent iron ion, as well as the equilibrium constant K of hydrofluoric acid and the equilibrium constants $K_1$ and $K_2$ of iron fluoride complexes. The equilibrium constants K, $K_1$ and $K_2$ are stored in the processing unit beforehand and can be modified as appropriate.

In the above-described example of analysis of free fluorine in a hydrofluoric acid-containing pickling solution for a stainless steel, only iron ion is considered as a metallic ion, though there are also other metallic ions such as chromium ion and nickel ion coexisting in the solution. However, it does not pose any problems to the operation to assume that only iron ion is a metallic ion, and to use the free fluorine concentration value obtained by analysis based on the assumption, since the amounts of these other coexisting metallic ions are negligibly small. If it is necessary to have a free fluorine concentration with better analytical accuracy, the concentrations of other metallic ions such as chromium ion and nickel ion as well as the equilibrium constants of fluorides of these metals can be added to the processing.

It is noted that in the present invention, the units for expressing a free fluorine concentration, a total fluorine concentration, a total acid concentration or an iron ion concentration are not limited to mol/L, and arbitrarily chosen units of concentration can be used.

The present invention will be explained in still greater detail based on the examples below.

EXAMPLE 1

The free fluorine in a hydrofluoric acid-containing solution was analyzed in accordance with the analytical method and analyzing apparatus for analyzing free fluorine shown in FIG. 1.

Regarding the hydrofluoric acid-containing solution, a nitric acid/hydrofluoric acid pickling solution for a stainless steel was chosen as a target. More specifically, a hydrofluoric acid-containing solution prepared by putting hydrofluoric acid, nitric acid and iron ion in the amounts (concentrations) shown in Table 1 was used.

First of all, the concentrations of total fluorine, total acid and iron ion, in the nitric acid/hydrofluoric acid solution were quantitatively measured by the lanthanum nitrate precipitation titration method, the iron reduction-neutralization titration method and the iron-EDTA complex absorptiometric method, respectively.

Next, the free fluorine concentration (HF concentration+ F$^-$ concentration) was determined by using an analytical value of total fluorine concentration $\alpha$, an analytical value of total acid concentration $\beta$, an analytical value of iron ion concentration $\gamma$, the values having been thus obtained, and the equilibrium constants K, $K_1$ and $K_2$ obtained by above-described equations (1)–(6) and (10)–(12). Results thus obtained are shown in Table 1.

While the data in Table 1 are represented in g/L, the free fluorine concentration was obtained in mol/L, by converting the concentrations of total fluorine, total acid and iron ion to those in mol/L when processing with the equations (1)–(12).

As shown in Table 1, it was found possible to analyze free fluorine in a stable manner without being affected by the coexistent iron, with a method and apparatus having excellent accuracy, by determining the free fluorine concentration through calculation from analytical values of total fluorine concentration, total acid concentration and iron ion concentration, as well as the equilibrium constant K of hydrofluoric acid and the equilibrium constants $K_1$ and $K_2$ of iron fluoride complexes.

TABLE 1

| Sample No. | Amount of added materials | | | Result of analysis/processing Free fluorine (g/l) |
| --- | --- | --- | --- | --- |
| | Hydrofluoric acid (g/l) | Nitric acid (g/l) | Iron ion (g/l) | |
| 1 | 10 | 130 | 20 | 2 |
| 2 | 20 | 130 | 20 | 9 |
| 3 | 30 | 130 | 20 | 18 |
| 4 | 40 | 130 | 20 | 26 |

According to the present invention, the analytical value of free fluorine does not change as time passes, since the analytical values of total fluorine concentration, total acid concentration and metallic ion concentration necessary for the analysis of free fluorine are not affected by the passage of time. Therefore, accuracy in analysis of free fluorine is improved so that the pickling efficiency can be improved, and the cost in pickling can be reduced in the operation.

EXAMPLE 2

Comparative Example

Analysis of free fluorine was performed with the same hydrofluoric acid-containing solution as the sample No. 2 in Example 1, and in accordance with the conventional iron-acetylacetone complex fading absorptiometric method.

Figure 2:
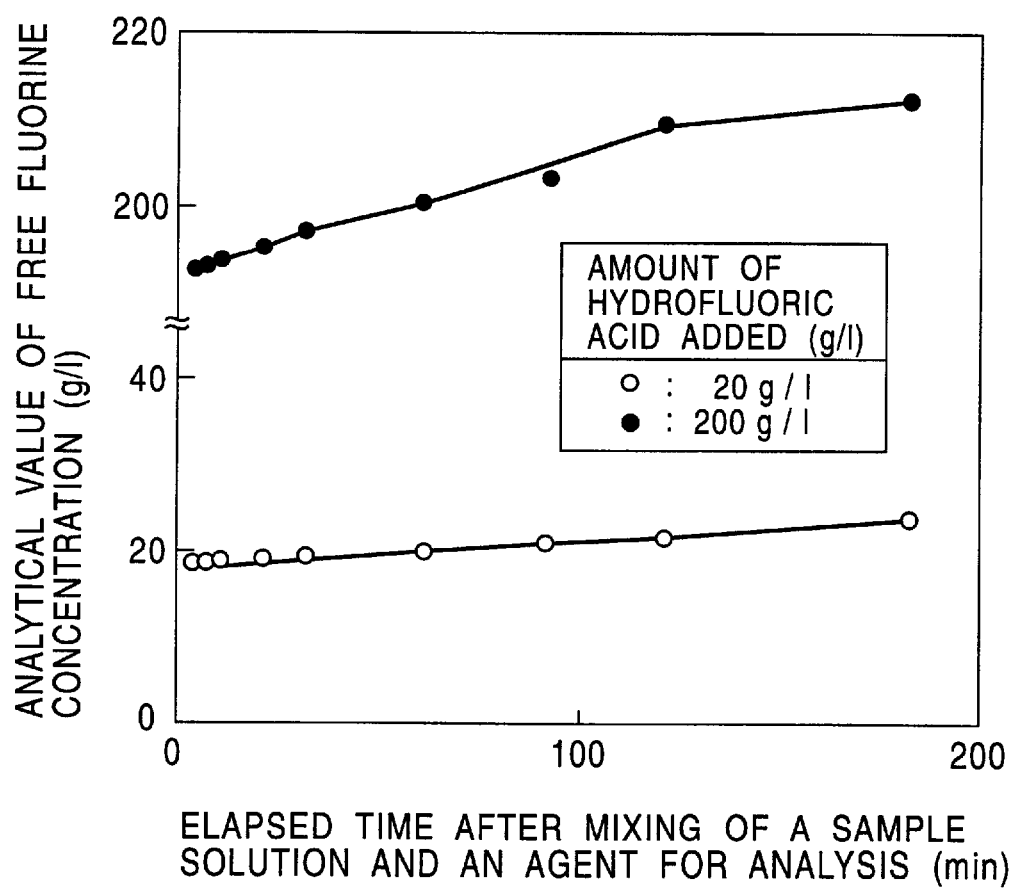
FIG. 2 is a graph showing changes of analytical values of free fluorine in hydrofluoric acid-containing solutions measured by the iron-acetylacetone complex fading absorptiometric method with respect to time.

Analysis of free fluorine was performed also with a hydrofluoric acid-containing solution prepared by putting 200 g/L of hydrofluoric acid in the sample No. 2 in Example 1, and in accordance with the same absorptiometric method. It is noted that the analyses were repeated on the same hydrofluoric acid-containing solutions. FIG. 2 shows changes of the analytical values thus obtained with the passage of time.

As shown in FIG. 2, there was a tendency that the analytical values were increased as time passed after mixing the analytical agents with the sample solutions. This tendency was heightened as the addition of hydrofluoric acid was increased, and the values thus obtained were sometimes higher than the amounts actually added.

This is considered to be caused by the fact that when the iron-acetylacetone complex is dissociated by fluorine ion, various forms of the complex with different absorption coefficients are generated as time passes, by the influence of iron in a sample solution.

Regarding the hydrofluoric acid-containing solution in the above-described example 1, a nitric acid/hydrofluoric acid pickling solution for a stainless steel was chosen as a target, and a hydrofluoric acid-containing solution comprising hydrofluoric acid, nitric acid and iron ion was actually used. However, based on he techniques involved in the present invention, it is possible to apply the present invention to the analysis of free fluorine in a hydrofluoric acid-containing solution having various metallic ions other than iron, for example, aluminum ion.

According to the present invention, it is possible to analyze free fluorine in a hydrofluoric acid-containing solution without being affected by a coexistent metal and by the passage of time, by using a method and apparatus having excellent accuracy. Thus, it is possible, for example, to accurately control the concentration of free fluorine in a hydrofluoric acid-containing mixed acid pickling solution at the production site of a stainless steel with a result that improvement in descaling capability as well as reduction in the amount of chemical materials can be achieved.

While the present invention has been described above in connection with several preferred embodiments, it is to be expressly understood that those embodiments are solely for illustrating the invention, and are not to be construed in a limiting sense. After reading this disclosure, those skilled in this art will readily envision insubstantial modifications and substitutions of equivalent materials and techniques, and all such modifications and substitutions are considered to fall within the true scope of the appended claims.

What is claimed is:

1. A method for analyzing a total concentration of HF and $F^-$ in a solution containing hydrofluoric acid and at least one species of metal ion, comprising the steps of:
   obtaining analytical values by quantitatively analyzing a total fluorine concentration by a precipitation titration method employing lanthanum nitrate, an acid concentration by reducing a metal followed by neutralization titration, and a metal ion concentration by an absorptiometry; and
   calculating from said analytical values, an equilibrium constant of hydrofluoric acid and an equilibrium constant of metal fluoride the total concentration of HF plus $F^-$.

2. The method as claimed in claim 1, wherein said absorptiometry is an absorptiometry of a metal-EDTA complex.

3. The method as claimed in claim 1, wherein said solution is a hydrofluoric acid-containing mixed acid solution and the acid concentration is a total acid concentration.

4. The method as claimed in claim 1 or 3, wherein said solution is a pickling solution for a stainless steel.

5. An apparatus for analyzing a total concentration of HF and $F^-$ in a solution containing hydrofluoric acid and at least one species of metal ion, comprising:
   a total fluorine concentration analyzing unit for analyzing a total fluorine concentration in said solution to output a first analytical value;
   an acid concentration analyzing unit for analyzing an acid concentration in said solution to output a second analytical value;
   a metal ion concentration analyzing unit for analyzing a metal ion concentration in said solution to output a third analytical value; and
   a processing unit that receives said first, second and third analytical values and calculates a concentration of said total concentration of HF and $F^-$ based on equilibrium constants of hydrofluoric acid and metal fluoride,
   wherein said total fluorine concentration analyzing unit is an analytical unit employing a precipitation titration method using lanthanum nitrate, said total acid concentration analyzing unit is an analytical unit for reducing a metal followed by neutralization titration, and said metallic ion concentration analyzing unit is a unit for analyzing a metal-EDTA complex by absorptiometry.

6. The apparatus as claimed in claim 5, wherein said apparatus for analyzing free fluorine further comprises a sampling unit to supply a sample to each of said concentration analyzing units.

7. An apparatus for analyzing total concentration of HF and $F^-$ in a solution containing hydrofluoric acid and at least one species of metal ion, comprising:
   means for analyzing a total fluorine concentration in said solution to output a first analytical value;
   means for analyzing an acid concentration in said solution to output a second analytical value;
   means for analyzing a metal ion concentration in said solution to output a third analytical value; and
   means for receiving said first, second and third analytical values and for calculating a concentration of said total concentration of HF and $F^-$ based on equilibrium constants of hydrofluoric acid and metal fluoride.

* * * * *